Figure 1:
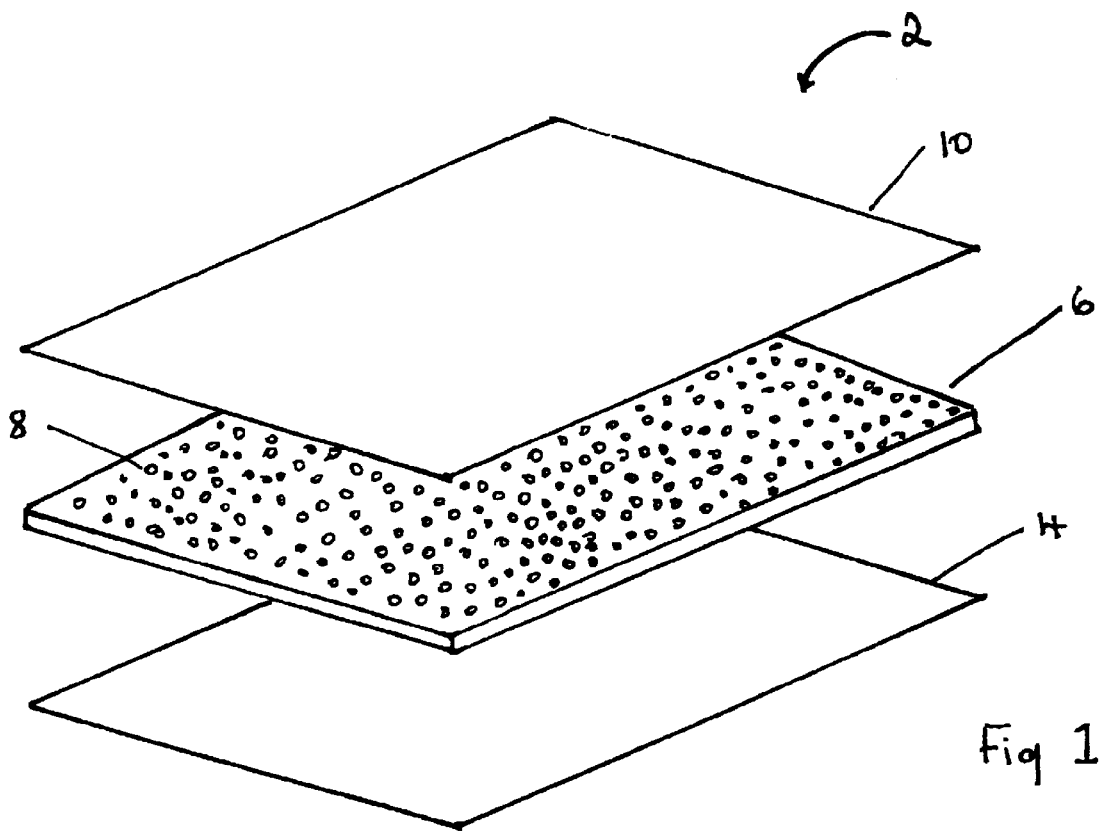

United States Patent

Court et al.

Patent Number: 5,941,840
Date of Patent: Aug. 24, 1999

[54] MULTI-LAYERED WOUND DRESSING

[75] Inventors: Andrew D. Court, South Wirral; Mark G. Rippon, Wrexham; Elizabeth Jacques, Chester, all of United Kingdom

[73] Assignee: Bristol-Myers Squibb Company, New York, N.Y.

[21] Appl. No.: 09/133,349

[22] Filed: Aug. 13, 1998

[30] Foreign Application Priority Data

Aug. 16, 1997 [GB] United Kingdom ............... 9717357

[51] Int. Cl.⁶ .................................................. A61F 13/00
[52] U.S. Cl. ............................. 602/47; 602/56; 602/41
[58] Field of Search ........................... 602/41, 56, 47

[56] References Cited

U.S. PATENT DOCUMENTS 4,341,207  7/1982  Steer et al. .
4,667,665  5/1987  Bianco et al. .
5,465,735  11/1995  Patel .
5,681,579  10/1997  Freeman .

FOREIGN PATENT DOCUMENTS

| | | |
|---|---|---|
| 0478011 | 4/1992 | European Pat. Off. . |
| 0633009 | 1/1995 | European Pat. Off. . |
| 2093703 | 9/1982 | United Kingdom . |
| 9000041 | 1/1990 | WIPO . |
| 9519795 | 7/1995 | WIPO . |
| 9625958 | 8/1996 | WIPO . |

*Primary Examiner*—Richard J. Apley
*Assistant Examiner*—Kelvin Hart
*Attorney, Agent, or Firm*—John M. Kilcoyne; Theodore R. Furman, Jr.

[57] ABSTRACT

The present invention relates to a multi-layered wound dressing particularly for use as a dressing on highly exudating wounds.

11 Claims, 1 Drawing Sheet

MULTI-LAYERED WOUND DRESSING

The present invention relates to a multi-layered wound dressing particularly, but not exclusively, for use as a dressing on highly exudating wounds.

It is known to make wound dressings having a continuous wound and skin contacting layer comprising a blend of one or more water soluble or water swellable hydrocolloids and a viscous substance such as polyisobutylene. The wound and skin contacting layer is a fluid-interactive adhesive which absorbs exudate while at the same time adhering the dressing to the skin surrounding the wound. Such fluid interacting adhesives are disclosed in, for example, U.S. Pat. No. 4,538,603 to Pawelchak et al. A disadvantage of such dressings is that absorption of exudate by the fluid-interactive adhesive may not be fast enough to avoid maceration in a heavily exudating wound. This can be due to a mechanism known as gel-blocking where the formation of a gel by the adhesive on absorption of exudate blocks the absorption of further exudate and therefore limits the absorptive capacity of the dressing. However, an advantage of such dressings is that they bring hydrocolloids into direct contact with the wound. Hydrocolloids and other gelling polymers are believed to have wound healing properties and on contact with exudate form a gel which creates a non-adherent contact with the wound.

In EP-A-0617938 a multi-layer dressing for highly exudating wounds is proposed in which the wound contact layer is a non-continuous polymeric support having hydrocolloids incorporated therein. The non-continuous nature of the polymeric support provides pathways for the rapid uptake of wound fluids into an absorbent layer overlying the support. A disadvantage of such dressings is that because hydrocolloids are incorporated into the wound contacting layer their ability to rapidly absorb exudate is limited despite the pathways for wound fluids.

EP-A-0304536 discloses an occlusive wound dressing comprising a continuous wound contact layer which is an adhesive permitting prolonged adhesion of said wound dressing to the skin, a fabric layer bonded to the adhesive layer, a hydrophilic absorbent polymeric layer applied to said fabric layer, said polymeric layer having been applied to or impregnated within the fabric layer, and an occlusive backing layer. The absorbent polymeric layer can comprise carboxymethyl cellulose.

There is thus a need for a wound dressing which is capable of absorbing exudate at the rate it is produced by a heavily exudating wound and which also delivers hydrocolloids to the wound.

We have now developed a multi-layered wound dressing which alleviates the above problems and there is provided by the present invention a multi-layered wound dressing comprising:

(a) a non-continuous wound contact layer which is substantially free of hydrocolloids and adhesives;

(b) an absorbent layer overlying said wound contact layer;

(c) a coating of a gelling polymer on a surface of said absorbent layer distant from the wound contacting layer; and (d) a hydrophobic layer overlying said coating of gelling polymer.

We have found that wound dressings according to the invention have a lower than expected adherency to the wound and this is thought to be due to the delivery of gelling polymer to the interface between the dressing and the wound. In particular this is thought to be the mechanism responsible for lower than expected adherency in dressings according to the invention where the gelling polymer is a hydrocolloid or other gelling polymer. This is truly surprising since the gelling polymers are not in direct contact with the wound but separated from it by the wound contact layer and absorbent layer. This unexpected finding also gives the dressings according to the invention the advantage that the benefits of hydrocolloids, alginates or other gelling polymers are obtained without compromising the absorption characteristics of the dressing.

The wound contact layer is non-continuous to allow exudate to pass through to the absorbent layer as quickly as possible and preferably contains no adhesive to stick the dressing to the wound and surrounding skin. Typically the wound contact layer is a film with perforations or slits to allow exudate passage. The film preferably is thermoformable, conformable polyester, polypropylene, polyethylene, or bi-component polyethylene/ethylvinylacetate, or any other suitable polymer.

The absorbent layer is present to transport fluid away from the wound and absorb it while maintaining dressing structure. The absorbent layer is preferably a non-woven fabric comprising a blend of suitable fibers such as cotton, viscose or bi-component fibers. For example, the layer is DANAKLON ES-C-PHIL™, a polyolefin bi-component fiber available from DANAKLON of Varde, Denmark. The fibers suitable for use in the present invention can be natural or synthetic and can be selected from polyesters and polyacrylates, but are preferably cellulosic fibers such as viscose rayon, multi-limbed viscose, cotton, or regenerated cellulose, or fibers having a higher absorbency than most textile fibers such as the multi-limbed cellulose fibers as described in EP-A-301874. More preferably the absorbent layer comprises from 50% to 70% by weight of viscose fibers, from 15% to 50% of polyester fibers and optionally from 0% to 20% by weight of a bi-component fiber comprising polypropylene and polyethylene. Most preferably the absorbent layer comprises 63% by weight of viscose, 25% by weight of polyester and 12% of a bi-component fiber.

A gelling polymer is one which upon the uptake of wound exudate becomes moist and slippery and/or gelatinous. In particular, in the context of the present invention, the gelling polymer is one which contributes to the wound dressing having lower than expected adherency to the wound and this is thought to be due to the delivery of gelling polymer to the interface between the dressing and the wound. The gel can be of the type which retains its structural integrity on absorption of exudate, or it can be of the type which loses its form and becomes a viscous solution on absorption of exudate. The gelling polymer is preferably selected from the group including hydrocolloids such as sodium carboxymethylcellulose, or pectin, sodium alginate, or sodium/calcium alginate, chitosan, carrageenan, xanthan, gellan, polyaspartic acid, polyglutamic acid, hyaluronic acid or salts or derivatives thereof, or other polysaccharides or other gums. The gelling polymer may be sprinkled on the upper surface of the absorbent layer, that is the layer most distant from wound contact layer. The gelling polymer can be mixed with an adhesive so that during manufacture of the dressing, the application of heat and/or pressure causes the absorbent layer and the hydrophobic layer to laminate together. The coating density of the gelling polymer is preferably about 80 to 120 g/m$^2$.

The hydrophobic layer helps to prevent strike through of exudate and hinders the ingress of liquid. The hydrophobic layer is preferably a non-woven hydrophobic viscose, for example a random laid, chemically bonded, oil and water repellent treated, non-woven viscose available from Lantor, UK.

Figure 2:

Preferred embodiments of the present invention will now be described by way of example with reference to the accompanying drawings, in which:

FIG. 1 is a schematic diagram of a multi-layered wound dressing according to the invention; and FIG. 2 shows a side view of the dressing of FIG. 1.

Referring now to FIG. 1 of the drawings, the multi-layered dressing (2) comprises a non-continuous wound contact layer (4), an absorbent layer (6) overlying said wound contact layer (4), a coating of gelling polymer (8) overlying said absorbent layer (6) and a hydrophobic layer (10) overlying said coating of gelling polymer (8). The wound contact layer (4) is preferably a noncontinuous polyethylene/ethylene vinyl acetate film. The absorbent layer (6) is preferably a blend of 63% viscose fibers, 25% polyester fibers and 12% of polypropylene/polyethylene bi-component fibers. The coating of gelling polymer (8) is preferably a blend of powdered cyclic polyester and sodium carboxymethyl cellulose in the ratio 1:3 by weight. The hydrophobic layer (10) is preferably a non-woven hydrophobic viscose cover stock.

The dressing will typically be made in three sizes: 55×55 mm square, 105×105 mm square and 205×105 mm rectangular, all dressings being about 2.5 mm thick.

The invention will now be illustrated by means of the following examples:

EXAMPLE 1

A dressing according to the invention was made first by making the absorbent layer by blending a mixture of 63% viscose fibers Sarille O® available from Courtaulds, 25% polyester fibers Trevira Type 290 available from Hoechst and 12% polypropylene/polyethylene bi-component fibers DANAKLON ES-C-PHIL available from DANAKLON, and then carding to form a web.

The web was then cross laid, needled and thermobonded to form a coherent, non-woven fleece. A wound contact layer consisting of a film of perforated polyethylene, ethylvinylacetate 909 Net available from Smith and Nephew or Delnet available from AET was then positioned on the lower surface of the absorbent fleece. A powder blend of a cyclic polyester DT135 available from Dritex and sodium carboxymethyl cellulose, Cekol 50,000G3 available from Metsa Serla in the proportions 1:3 by weight was then sprinkled on the upper surface of the absorbent fleece at a coating density of about 100 g/m². This was then covered by a non-woven, hydrophobic viscose cover stock. The whole dressing was then laminated together by the application of heat and pressure.

EXAMPLE 2

The action of the gelling polymer layer in a wound dressing according to the invention was studied in vitro by analyzing the bioadhesion of cells to the dressing. As background it should be appreciated that some dressings may induce damage to proliferating and migrating cells present in a wound. Fibroblasts or epithelial cells that are proliferating and migrating may adhere to the surface of a wound dressing and be removed when the dressing is changed thereby hindering the normal healing process rather than enhancing it. The dressings according to the present invention are believed to reduce bioadhesion to the wound by delivering gelling polysaccharide to the wound even though the gelling polymer is remote from the wound. This gives the advantage that the absorbency of the dressing is not limited, as it would be in a dressing where the entire wound contact layer was hydrocolloid or other polysaccharide or polymer, but the benefits of the presence of gelling polymers are obtained.

The bioadhesion of dermal equine fibroblasts to the dressing of the present invention and a commercially available wound dressing MELOLIN, a perforated film absorbent dressing available from Smith and Nephew, was studied by taking dermal tissue samples from both healing and non-healing areas of equine wounds.

Tissue samples were immediately transferred to a dish of Hank's balanced salt solution (Gibco) and washed. Samples were cut into 3–5 mm² pieces and placed into 25 cm² culture flasks (Nunc, Gibco) containing DMEM (Gibco), supplemented with 10% Foetal calf serum (Sigma), 20 mM Hepes buffer, 100 :g/ml gentamicin and 0.5 :g/ml amphotericin B (Gibco) in a 5% carbon dioxide in air, 37° C. environment (Cochrane, Freeman & Knottenbelt, 1996). Readiness for subculturing was determined by the extent of fibroblast cell outgrowth (5–10 days). Cells were farmed successively in a 1:4 split ratio to passage 3–8 for experimental use.

Healthy fibroblasts cells were harvested from stock dishes and plated out onto either plastic or type I collagen (Sigma) at 2 mg/ml or onto 6 multiwell plastic culture plates (Nunc) in triplicate at $2 \times 10^5$ cells/dish in lml DMEM supplemented with 10% foetal calf serum and 1% penicillin-streptomycin, 20 mM Hepes buffer (Gibco). Cells were left to attach for twenty-four hours, after which the cells were metabolically labeled.

The bioadhesion of dermal fibroblasts was investigated using a modified tritiated thymidine assay (Rudland et al., 1977; Muscolo D. L. & Ayerza M. A., 1996). Fibroblasts were plated out in 6 multiwell plates at $2 \times 10^5$ cells/35 mm well in 2 mls standard medium containing 10% FCS on either plastic or collagen. Cells were incubated for an initial period of 24 hours at 37° C. in a humid environment containing 5% $CO_2$ in air. The cells were labeled with 2:Ci/100:1 [6-$^3$H]-thymidine in DMEM with 10% FCS for bioadhesion analysis and incubated. Identical incubation volumes were maintained throughout the experiment to ensure an equal amount of radio label was added to each culture, and the cells were incubated for a further 24 hours.

Media was removed from the cultures and the cell layer was washed with Hanks balanced salt solution. The dressings were cut into 1 cm² pieces, soaked in fresh medium and applied to the cell cultures. The dishes containing the dressing according to the invention and MELOLIN dressings were incubated at room temperature for a total of 48 hours.

The dressings were removed from the cultures and placed into scintillation vials. The cell layer/gel was washed twice with 1 ml ice cold PBS. Proteins in the cell layer/gel were extracted with 1 ml 4M guanidium hydrochloride in 50 mM Tris/HCl buffer, pH 7.4 containing protease inhibitors (0.5 mM PMSF, 2 mM NEM, 2 mM EACA, 2 mM EDTA) at 4° C. for 24 hours (Herrick et al., 1996). Solubilized proteins were removed and the dish was scraped and rewashed with lml PBS. After the addition of scintillation fluid, the samples were counted in a liquid scintillation counter. The results were expressed as disintegrations per minute (dpm)×100.

The cell numbers in the triplicate parallel cultures were determined using trypsinization before and after treatment using a Neubauer counting chamber (Cochrane et al., 1996).

TABLE 1

Incorporation of 3H Thymidine distribution into dermal fibroblasts cultured for 24 hours (dpm × 100)

| Substrate Type | Dressing of Example 1 | | MELOLIN | |
|---|---|---|---|---|
| Plastic Dish | 13,369" | 677 | 40,967" | 3,575 |

TABLE 2

Fibroblast attachment to the dressing of Example 1 vs MELOLIN
Direct cell count of dermal fibroblasts cultured for 24 hours

| Substrate Type | Dressing of Example 1 | | MELOLIN | |
|---|---|---|---|---|
| Collagen Type 1 | 63,222" | 1,957 | 86,222" | 2,020 |
| Plastic Dish | 54,944" | 1,073 | 90,277" | 1,522 |

These results show the more equine dermal fibroblasts adhered to MELOLIN than to the dressing according to the invention. This strongly suggests that the dressing according to the invention is less likely to adhere to the wound and therefore reduces the risk of re-injury during dressing changes.

We claim:

1. A multi-layered wound dressing comprising:

(a) a non-continuous wound contact layer which is substantially free of hydrocolloids and adhesives;

(b) an absorbent layer overlying said wound contact layer;

(c) a coating of a gelling polymer on a surface of said absorbent layer distant from the wound contact layer; and (d) a hydrophobic layer overlying said coating of gelling polymer.

2. A multi-layered wound dressing as claimed in claim 1 wherein the coating of gelling polymer on the absorbent layer includes an adhesive.

3. A multi-layered wound dressing as claimed in claim 1 wherein the gelling polymer is a hydrocolloid.

4. A multi-layered wound dressing as claimed in claim 1 wherein the gelling polymer is selected from the group consisting of sodium carboxymethylcellulose, pectin, sodium alginate, sodium/calcium alginate, chitosan, carageenan, xanthan, gellan, polyaspartic acid, polyglutamic acid, hyaluronic acid or salts or derivatives thereof, other polysaccharides and other gums.

5. A multi-layered wound dressing as claimed in claim 1 wherein the absorbent layer is a non-woven fabric.

6. A multi-layered wound dressing as claimed in claim 1 wherein the wound contact layer is a film with perforations or slits to allow exudate passage.

7. A multi-layered wound dressing as claimed in claim 1 wherein the hydrophobic layer is a non-woven hydrophobic viscose.

8. A multi-layered wound dressing as claimed in claim 1 wherein the gelling polymer imparts low adherency to the dressing.

9. A multi-layered wound dressing as claimed in claim 1 wherein the gelling polymer is one which upon the uptake of wound exudate becomes moist and slippery and/or gelatinous.

10. A multi-layered wound dressing as claimed in claim 1 wherein the gelling polymer reduces adherency between the dressing and the wound.

11. A method of treating a wound comprising applying to said wound a multi-layered wound dressing as claimed in claim 1.

* * * * *